(12) United States Patent
Behe et al.

(10) Patent No.: US 10,953,114 B2
(45) Date of Patent: *Mar. 23, 2021

(54) MINI-GASTRIN ANALOGUE, IN PARTICULAR FOR USE IN CCK2 RECEPTOR POSITIVE TUMOUR DIAGNOSIS AND/OR TREATMENT

(71) Applicant: Paul Scherrer Institut, Villigen (CH)

(72) Inventors: Martin Behe, Gelterkinden (CH); Roger Schibli, Baden (CH)

(73) Assignee: Paul Scherrer Institut, Villigen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/157,961

(22) Filed: Oct. 11, 2018

(65) Prior Publication Data

US 2019/0240360 A1    Aug. 8, 2019

Related U.S. Application Data

(63) Continuation of application No. 15/034,943, filed as application No. PCT/EP2014/072697 on Oct. 23, 2014, now Pat. No. 10,130,724.

(30) Foreign Application Priority Data

Nov. 6, 2013   (EP) .................................... 13191807

(51) Int. Cl.
| | |
|---|---|
| A61K 51/08 | (2006.01) |
| A61K 38/22 | (2006.01) |
| G01N 33/574 | (2006.01) |
| C07K 14/575 | (2006.01) |
| C07K 14/595 | (2006.01) |
| C07B 59/00 | (2006.01) |
| C07K 1/13 | (2006.01) |
| C07K 7/08 | (2006.01) |

(52) U.S. Cl.
CPC ........ *A61K 51/088* (2013.01); *A61K 38/2207* (2013.01); *C07B 59/008* (2013.01); *C07K 1/13* (2013.01); *C07K 7/08* (2013.01); *C07K 14/57572* (2013.01); *C07K 14/595* (2013.01); *G01N 33/57484* (2013.01); *G01N 2333/726* (2013.01)

(58) Field of Classification Search
None
See application file for complete search history.

(56) References Cited

U.S. PATENT DOCUMENTS

| 4,650,787 A | 3/1987 | Schally et al. |
| 10,130,724 B2 * | 11/2018 | Behe .................... A61K 51/088 |

OTHER PUBLICATIONS

Laverman et al. "Comparative biodistribution of 12 111In-labelled gastrin/CCK2 receptor-targeting peptides" Eur. J. Nucl. Med. Mol. Imaging 38:1410-1416. (Year: 2011).*

Melicharova et al. "Preclinical evaluation of gastrin derivatives labelled with 111In: Radiolabelling, affinity profile and pharmacokinetics in rats" Biomed Pap Med Fac Univ Palacky Olomouc Czech Repub 157:XX (Year: 2013).*

Mather et al. "Selection of Radiolabeled Gastrin Analogs for Peptide Receptor-Targeted Radionuclide Therapy" J. Nucl. Med. 48: 615-622. (Year: 2007).*

Lee et al. "Peptides and Peptide Hormones for Molecular Imaging and Disease Diagnosis" Chem. Rev. 110:3087-3111. (Year: 2010).*

Thundimatdathil J "Cancer Treatment Using Peptides: Current Therapies and Future Prospects" J. Amino Acids 2012: Article ID 967347. (Year: 2012).*

Aloj et al., "In vitro and In vivo Evaluation of 111In-DTPAGlu-G-CCK8 for Cholecystokinin-B Receptor Imaging," J. Nucl. Med., 2004, 45(3):485-494.

Behr et al., "Cholecystokinin-B/gastrin receptor-targeting peptides for staging and therapy of medullary thyroid cancer and other cholecystokinin-B receptor-expressing malignancies," Seminars in Nuclear Medicine, Apr. 1, 2002, 32(2):97-109.

Gotthardt et al., "Added value of gastrin receptor scintigraphy in comparison to somatostatin receptor scintigraphy in patients with carcinoids and other neuroendocrine tumors," Endocrine-Related Cancer, Dec. 2006, 13(4):1203-1211.

Gotthardt et al., "Improved tumor detection by gastrin scintigraphy in patients with metastasized medullary thyroid carcinoma," Eur. J. Nucl. Med. Mol. Imaging, Nov. 2006, 33(11):1273-1279.

Kolenc-Peitl et al., "Highly Improved Metabolic Stability and Pharmacokinetics of Indium-111-DOTA-Gastrin Conjugates for Targeting of the Gastrin Receptor," Journal of Medicinal Chemistry, Apr. 28, 2011, 54(8):2602-2609.

Laverman et al., "Comparative biodistribution of 12 111In-labelled gastrin/CCK2 receptor-targeting peptides," European Journal of Nuclear Medicine and Molecular Imaging, Apr. 2, 2011, 38(8):1410-1416.

(Continued)

*Primary Examiner* — Sudhakar Katakam
*Assistant Examiner* — Zachary J Miknis
(74) *Attorney, Agent, or Firm* — Foley & Lardner LLP

(57) ABSTRACT

A gastrin analogue shows high uptake in CCK-2 receptor positive tumors and simultaneously a very low accumulation in the kidneys. This is achieved by a mini-gastrin analogue PP-F11 having the formula: PP-F11-X-DGlu-DGlu-DGlu-DGlu-DGlu-DGlu-Ala-Tyr-Gly-Trp-Y-Asp-Phe-$NH_2$, wherein Y is an amino acid replacing methionine and X is a chemical group attached to the peptide for diagnostic and/or therapeutic intervention at CCK-2 receptor relevant diseases. Very suitable compounds with respect to a high tumor to kidney ratio are mini-gastrin analogues with six D-glutamic acids or six glutamines. These compounds still possess a methionine which can be oxidized easily which is a disadvantage for clinical application under GMP due to the forms which may occur. The elimination of the methionine leads to a lower affinity to oxidation which in general favors the tumor-kidney-ratio. Ideally, the methionine is replaced by norleucine. This PP-F11N mini gastrin exhibits currently the best tumor-kidney-ratio and is the most promising candidate.

12 Claims, 4 Drawing Sheets

(56) References Cited

OTHER PUBLICATIONS

Laverman et al., "Targeting of a CCK2 receptor splice variant with 111In-labelled cholecystokinin-8 (CCK8) and 111In-labeled minigastrin," European Journal of Nuclear Medicine and Molecular Imaging, Oct. 13, 2007, 35(2):386-392.

Lee et al., "Peptides and Peptide Hormones for Molecular Imaging and Disease Diagnosis," Chem. Rev., May 12, 2010, 110:3087-3111.

Lehenberger et al., "The low-energy beta(−) and electron emitter (161)Tb as an alternative to (177)Lu for targeted radionuclide therapy," Nucl. Med. Biol., 2011, 38:917-924.

Mather et al., "Selection of Radiolabeled Gastrin Analogs for Peptide Receptor-Targeted Radionuclide Therapy," J. Nucl. Med., 2006, 48:615-622.

Reubi et al,. "Cholecystokinin(CKK)-A and CCK-B/Gastrin Receptors in Human Tumors," Cancer Research, Apr. 1, 1997, 57:1377-1386.

Reubi et al., "Peptide-Based Probes for Cancer Imaging," J. Nucl. Med., 2008, 49:1735-1738.

Reubi et al., "Unexpected High Incidence of Cholecystokinin-B/Gastrin Receptors in Human Medullary Thyroid Carcinomas," Int. J. Cancer, 1996, 67:644-647.

Roosenburg et al,. "Radiolabeled CCK/gastrin peptides for imaging and therapy of CCK2 receptor-expressing tumors," Amino Acids, Mar. 3, 2010, 41(5):1049-1058.

Sosabowski et al., "Targeting of CCK-2 Receptor-Expressing Tumors Using a Radiolabeled Divalent Gastrin Peptide," J. Nucl. Med., 2009, 50:2082-2089.

Thundimadathil, J., "Cancer Treatment Using Peptides: Current Therapies and Future Prospects," Journal of Amino Acids, 2012, vol. 2012, Article ID 967347, 1-13.

Behe et al., "Cholecystokinin-B (CCK-B)/Gastrin Receptor Targeting Peptides for Staging and Therapy of Medullary Thyroid Cancer and Other CCK-B Receptor Expressing Malignancies," Biopolymers (Peptide Science), 2002, 66:399-418.

Krošelj et al., abstract of "Comparison of DOTA-coupled minigastrin analogues and corresponding Nle congeners," European Journal of Nucl. Mol. Imaging (2012), 39 (Suppl. 2), pp. S533-S534, P0813.

* cited by examiner

PP-F11:
DOTA-*DGlu-DGlu-DGlu-DGlu-DGlu-DGlu*-Ala-Tyr-Gly-Trp-Met-Asp-Phe-NH2

PP-F11N:
DOTA-*DGlu-DGlu-DGlu-DGlu-DGlu-DGlu*-Ala-Tyr-Gly-Trp-Nle-Asp-Phe-NH2

MINI-GASTRIN ANALOGUE, IN PARTICULAR FOR USE IN CCK2 RECEPTOR POSITIVE TUMOUR DIAGNOSIS AND/OR TREATMENT

CROSS-REFERENCE TO RELATED APPLICATIONS

This application is a Divisional of U.S. application Ser. No. 15/034,943, which is the U.S. National Stage application of PCT/EP2014/072697, filed Oct. 23, 2014, which claims priority from European application EP 13191807.0, filed Nov. 6, 2013.

BACKGROUND OF THE INVENTION

Field of the Invention

The present invention relates to a mini-gastrin analogue and to its use in CCK2 receptor positive tumor diagnosis and/or treatment.

G protein-coupled receptors (GPCR) are used as target proteins for radiolabelled peptides since the early 90's. The somatostatin receptor was the prototype for radionuclide imaging and therapy with peptides (Lit) resulting in a clinical first line therapies for neuroendocrine tumors with Y-90 and Lu-177 labelled derivatives of octreotide (Lit). Several radiolabelled peptides were tested for the possibility to target overexpressed GPCR on tumours including gastrin realising peptide analogues (GRP), glucagon-like peptide 1 analogues (GLP-1), neurotensin analogues (NT) or neuropeptide Y analogues (NPY) (Mäcke, Reubi J Nucl Med 2008; 49:1735-1738). An additional very interesting target is the cholecystokinin-2 receptor (CCK-2 R). This receptor is mainly expressed on medullary thyroid carcinomas (MTC), small cell lung cancers (SCLC) and stromal ovarial tumors (Reubi, Int J Cancer. 1996 and Reubi, Cancer Res. 1997). Radiolabelled gastrin analogues are good candidates for targeting imaging and therapy. It was shown that In-111 labelled gastrin analogues are superior for detecting MTC compared to OctreoScan-111 and give additional information on neuroendocrine tumours particularly if they are negative in somatostatin receptor scintigraphy (Endocr Relat Cancer. 2006 December; 13(4):1203-11. Eur J Nucl Med Mol Imaging. 2006 November; 33(11):1273-9).

But due to the high kidney uptake the radiolabelled peptides could not be used for therapy. The high kidney uptake is correlated with the six negatively charged glutamic acids. 12 gastrin related compounds were designed, synthesised and compared as 111In labelled compounds. The best compounds with respect to a high tumour to kidney ratio are the mini-gastrins with six D-glutamic acids or six glutamines. These compounds still possess a methionine which can be oxidised easily. This is a disadvantage for clinical application because the receptor affinity is dramatically decreased after oxidation of the methionine and the production under GMP may be hampered dramatically.

A high potential for a significant improvement of the therapy and the image generation with patients having metastasized medullary thyroid carcinomas (MTC), small cell lung cancers (SCLC) and further CCK-2 receptor positive tumours has a specific labelling of the tumour cells with radio-labelled gastrin analogue. Basis for this finding is the proof of an over-expression of the respective CCK-2 target receptor at 92% of the investigated MTC, said proof being yielded by in-vitro studies [Reubi 1997]. Furthermore, the same working group identified the same over-expression of the CCK-2 target receptor at 57% of small cell lung cancers, 65% of astrocytomes and 100% of stromal ovarial tumours.

First therapy studies (phase 0 study) had been executed at eight patients having advanced metastasized medullary thyroid carcinomas. For two patients a partial remission was achieved, four patients showed a stabilization of the formerly strong progressive course of the cancer disease MTC after a therapy with $^{90}$Y-labelled mini-gastrin analogue. This study had to be stopped due to the nephrotoxicity of the therapy in terms of a strong accumulation of the substances used in said assay in the kidneys.

With support of the European COST initiative (European Cooperation in Science and Technology), in the meantime a plurality of significantly improved radio-labelled gastrin analogue have been synthesized by various working groups and have been investigated for their characteristics. As compared to the old gastrin analogue, these younger substances possess a significantly higher tumor-to-kidney ration with respect to the absorption in human tissue [Laverman 2011, Polenc-Peitl 2011, Ocak 2011, Fani 2012]. Currently, out of these younger gastrin analogues, $^{177}$Lu-PP-F11 (the linear mini-gastrin analogue with six D-Glu residues, hereinafter PP-F11) exhibited best properties for future radio nuclide therapy due to its high favorable accumulation in the tumor accompanied by a low accumulation in the kidneys.

BRIEF SUMMARY OF THE INVENTION

It is therefore the objective of the present invention to provide gastrin analogue which show even better accumulation in CCK-2 receptor positive tumours by simultaneously very low accumulation in the kidneys.

This objective is achieved according to the present invention by a mini-gastrin analogue PP-F11 having the formula: PP-F11-X-DGlu-DGlu-DGlu-DGlu-DGlu-DGlu-Ala-Tyr-Gly-Trp-Y-Asp-Phe-NH$_2$, wherein Y stands for an amino acid replacing methionine and X stands for a chemical group attached to the peptide for the purpose of diagnostic and/or therapeutic intervention at CCK-2 receptor relevant diseases.

In particular, very suitable compounds with respect to a high tumour to kidney ratio are mini-gastrin analogues with six D-glutamic acids or six glutamines. These compounds still possess a methionine which can be oxidised easily which is a disadvantage for clinical application under GMP due to the forms which may occur. Therefore, the replacement of the methionine by a non oxidizable isosteric amino acids but retaining the biological activity leads to a compound with no oxidation potential. This avoids the oxidation during storage and production which could be lead to lower affinity compound resulting in a low tumor to kidney ratio.

In a preferred embodiment of the present invention, the methionine is replaced by norleucine. This so-called PP-F11N mini gastrin exhibits currently the best tumor-to-kidney and is therefore the most promising candidate for clinical applications. With respect to radio cancer treatments, X may stand for a radio nuclide including the attachment group like a chelator for radiometals such as $^{177}$Lu or $^{90}$Y or $^{111}$In, or a prostethic group for non-metals like F-18 or radioiodines. In order to improve the medical imaging, the X may for an optically active chemical compound, such AlexaFluor® 647, IRDye 680RD or DY-700 and for optical therapeutic application it may be a photosensitizer like Photofrin, Forscam or Photochlor. For both application the active chemical compound may be a optical active nano-particle. In order to support the chemotherapeutic intervention, X may stand for a chemotherapeutic active compound, such as gemcitabine, doxorubicine or cyclophosphamide. The delivery of the described agents may be done by a nanoparticles or liposome as X whereas they are loaded with chemotherapeutic agents.

With respect to the use of the inventive mini gastrin, a diagnostic intervention at CCK-2 receptor relevant diseases and/or a therapeutic intervention at CCK-2 receptor relevant diseases is foreseen.

BRIEF DESCRIPTION OF THE SEVERAL VIEWS OF THE DRAWING

Preferred embodiments of the present invention are hereinafter described in more detail with respect to the attached drawings which depict in.

DESCRIPTION OF THE INVENTION

Figure 1:
FIG. 1 the structural design of PP-F11N starting from a mini-gastrin analogue PP-F11 being arised from the COST initiative.

FIG. 1 illustrates the mini-gastrin analogue PP-F1u that has been derived from the COST initiative mentioned above. The modified mini-gastrin analogue PP-F11N has been achieved by the exchange of the oxidizable amino acid methionine with norleucin. DOTA stands for 1,4,7,10-tetraazacyclododecane-1,4,7,10-tetraacetic acid which is an organic compound with the formula $(CH_2CH_2NCH_2CO_2H)_4$. The molecule consists of a central 12-membered tetraaza (i.e., containing four nitrogen atoms) ring. DOTA is used as a complexing agent, especially for lanthanide ions. Its complexes have medical applications as contrast agents and cancer treatments.

Figure 2:
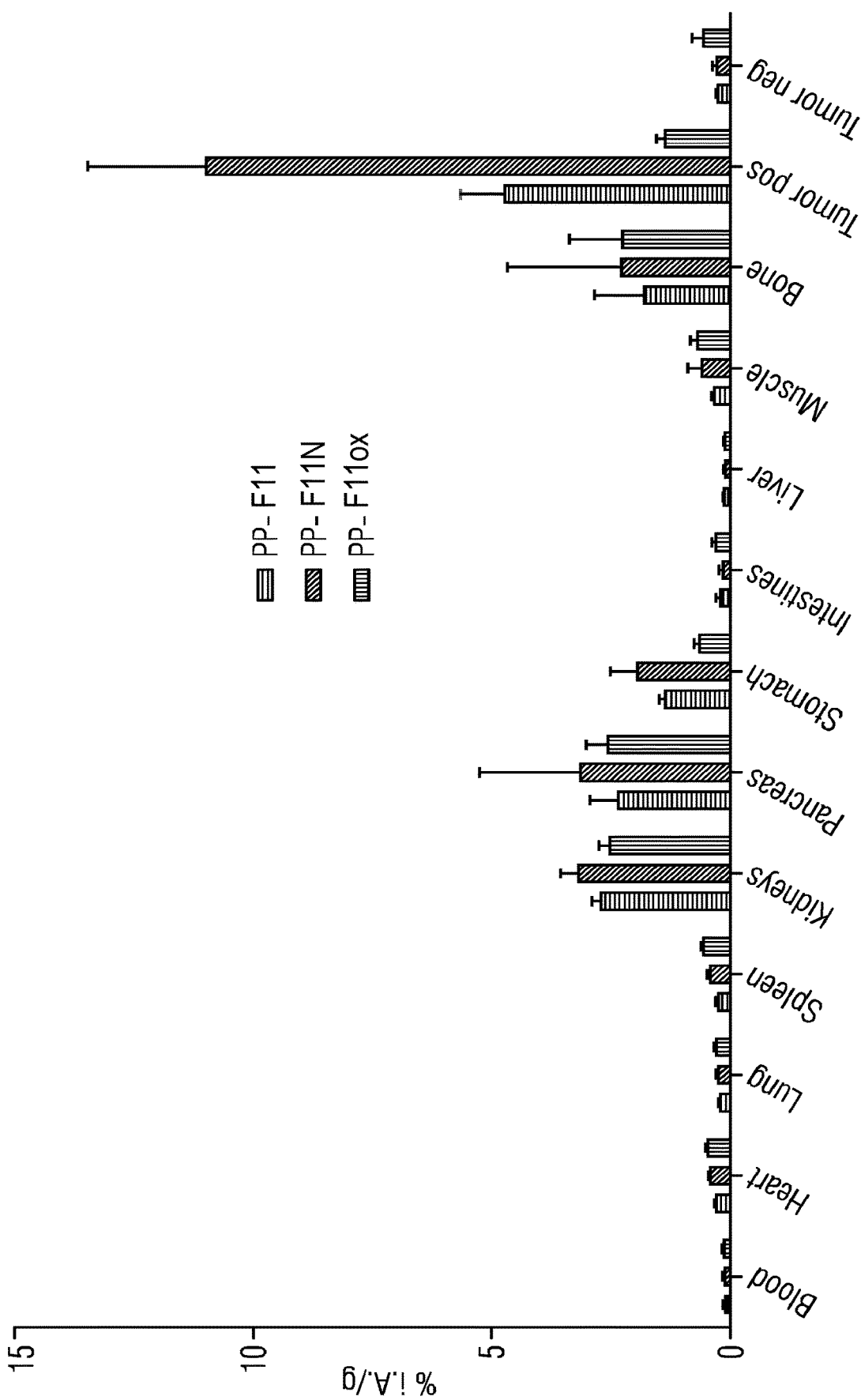
FIG. 2 the biodistribution of PP-F11, PP-F11N and PP-F11 ox (oxidized PP-F11) after four hours in the CD1 nu/nu mice model.

PP-F11N has been investigated according to the CD1 nu/nu mice model. As compared to PP-F11, the mini-gastrin analogue PP-F11N exhibited a significant higher tumor uptake which also leads to a very favorable tumor-noise ratio with very few accumulation in the kidneys. FIG. 2 illustrates the biodistribution of PP-F11, PP-F11N and oxidized PP-F11 ox (oxidized PP-F11) after 4 hours in the athymic CD1 nu/nu mice model. Tumour positive: with human CCK-2 receptor transfected A431 cells on one side of the mouse; tumor negative: CCK-2 receptor negative A431 cells on the other side of the mouse. The effect of the higher tumor uptake by the exchange of methionine with norleucine is specifically apparent with compounds having the DGlu6 sequence, different from compounds having a sequence with DGLn6 which is referred to as PP-F10.

Figure 3:
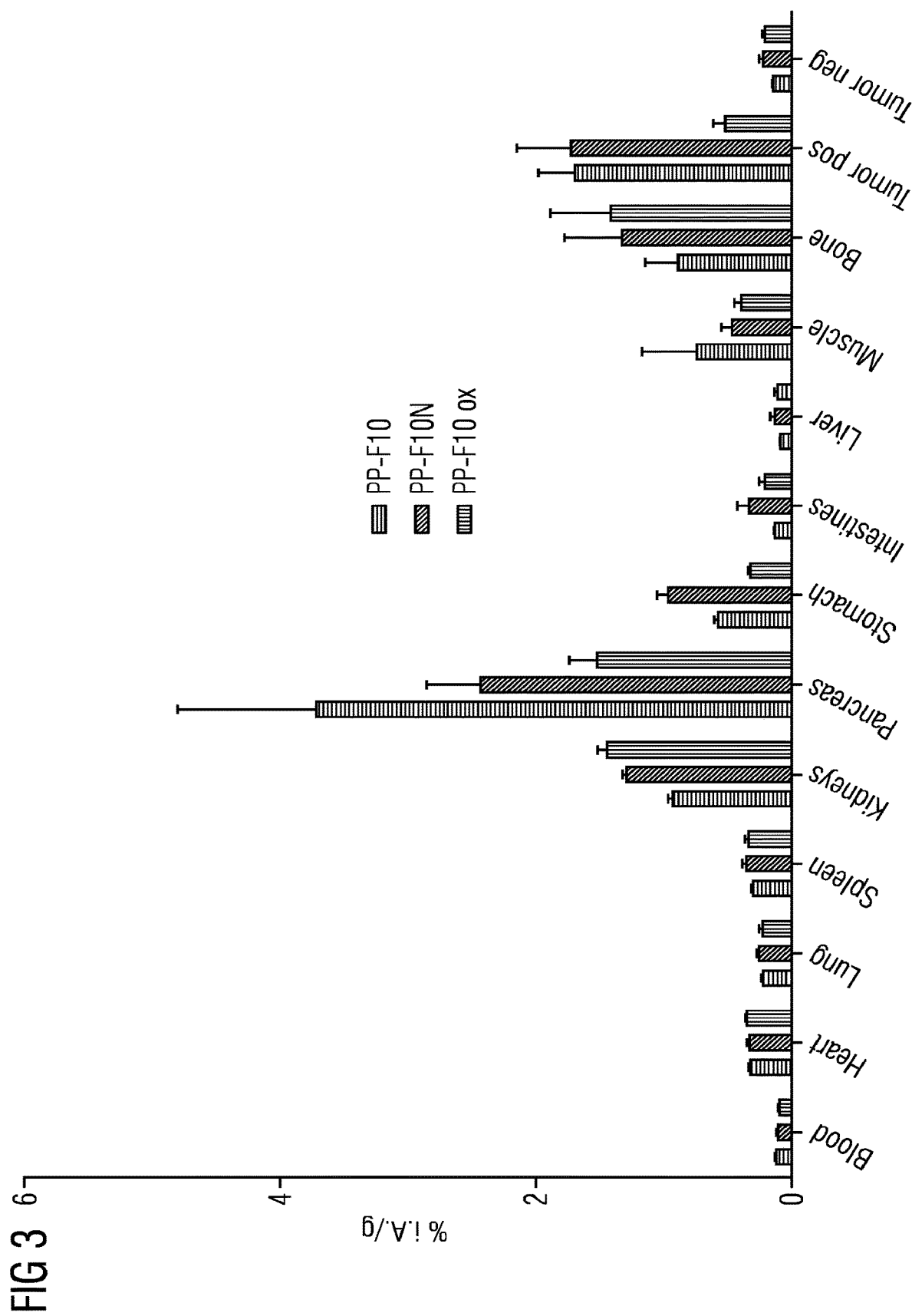
FIG. 3 the bio diversion of PP-F10, PP-F10N and PP-F10 ox (oxidized PP-F10) after four hours in the CD1 nu/nu mice model.

FIG. 3 shows the results for PP-F10 and PP-F10N and PP-F10 ox (oxidized PP-F10) in comparison to the results shown in FIG. 2. The structural formula of the PP-F10's is given below:

PP-F10: DOTA-DGln-DGln-DGln-DGln-DGln-DGln-Ala-Tyr-Gly-Trp-Met-Asp-Phe-$NH_2$
PP-F10N: DOTA-DGln-DGln-DGln-DGln-DGln-DGln-Ala-Tyr-Gly-Trp-Nle-Asp-Phe-$NH_2$;
PP-F10 ox: DOTA-DGln-DGln-DGln-DGln-DGln-DGln-Ala-Tyr-Gly-Trp-Met(ox)-Asp-Phe-$NH_2$.

A promising tumor uptake can therefore not be seen in FIG. 3 since other organs, such as the pancreas, the kidney and the bones take partially even higher doses than the targeted tumor.

Figure 4:
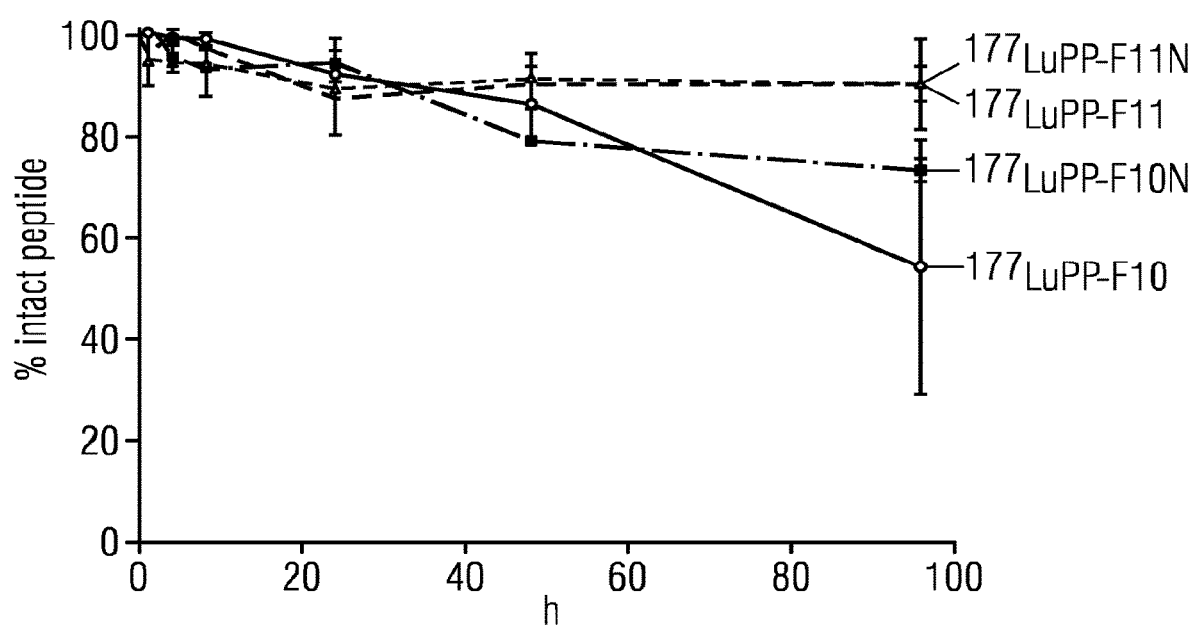
FIG. 4 the stability of diverse mini-gastrin analogues with the course of the time.

FIG. 4 illustrates the pharmacologic stability of PP-F11N as compared to PP-F11, PP-F10N and PP-F10 (all radiolabelled with $^{177}$Lu. The stability has been checked in human serum; the measurements of the metabolites have been executed by means of HPLC. The mini-gastrin analogue PP-F11N according to the present invention shows the highest pharmacologic stability of all probands.

Materials: The peptides (PP-F10, PP-F10N, PP-F11 and PP-11N) were synthesized by PLS (Heidelberg, Germany) by the Merrifield method. All the chemicals were purchased from Sigma-Aldrich (Buchs, Switzerland). A431 cells (cell line squamous cell carcinoma) were stably transfected with cDNA encoding for CCK2R or with empty vector ('mock-transfected')[1] and were a kind gift from L. Aloj (Naples). Lu-177 was purchased from ITG (Germany, Munich). The peptide conjugates were complexed with natural $^{nat}$Lu.

The labeling of the mini-gastrins has been executed under the following circumstances:

System for HPLC analysis:
System: Pump Varian Prostar 2030.01, Diode Array 330.71, Autosampler 410, Packard Radiomatic Flow-One\
Column: Stability 120 BS-C23 3 µm 150*4.6 mm, Dr. Maisch Gradient:

| Min | % H2O + 0.1% TFA | % ACN + 0.1% TFA |
|---|---|---|
| 0 | 90 | 10 |
| 3 | 90 | 10 |
| 15 | 5 | 95 |

System for the purification:
Pump 1: Waters 515, Pump 2: Hitachi L-7000, Knauer UV Detector K2510, Radio-Monitor Eberline, interface SS420X, EZstart
Rheodyne Manuel Injector
Column 1: Stability 120 BS-C23 3 µm 10*4.6 mm, Dr. Maisch
Column 2: Stability 120 BS-C23 3 µm 150*4.6 mm, Dr. Maisch

| Min | % H2O + 0.1% TFA | % ACN + 0.1% TFA | Valve 1 | Valve2 |
|---|---|---|---|---|
| 0 | 72 | 28 | Inject | Load |
| 3 | 72 | 28 | Inject | Inject |
| 20 | 60 | 40 | | |
| 25 | 5 | 95 | | |
| 35 | 5 | 95 | | |

Products:
Lu-177: lot Lu-12-052-01/121042, Activity 2 GBq/200 µl 0.04M HCL, itg (ITM AG)
PP-F11N: 0.25 mM $H_2O$ solution
Ammonium solution: Sigma-Aldrich metal free
Na Ascorbate: Sigma-Aldrich
HCl 30%: sigma-Aldrich nmetal free
$H_2O$: from Milipore system Biotel
Labelling of the peptide PPF11N with Lu-177:
The Labelling of Lu-177 with the PPF-11N was made with an isotope:peptide ratio of 1:47.
Mixture of Lu-177 with peptide to an eppendorf 1.5 ml lw binding:

20 µl Lu-177 (190 MBq)
5 µl Ammonium ascorbate 0.7M
50 µl PPF-11N 0.25 mM
5 µl HCl 0.04M The mixture was heated for 20 minutes at 95° C.

Afterwards the complex was purified and checked with HPLC methods.

Two syntheses were achieved in parallel

Purification of labelling peptide with HPLC

The two labellings reaction was injected into a 2 D HPLC.

Description of 2D HPLC:
  First step: inject the product into the loop with a rheodyne manual injector and push the product with a first pump through the column 1. The product is transferred from loap to the column 1 and is washed with $H_2O+0.1TFA$.
  Second Step: start the gradient with a second pump and change the position of the valve to connect in serial the column 1 and column 2.
  The product is push from column 1 in column 2. The excess of peptide is separed of the labeled Lu-177-PPF11N in the column 2 and is collected with a fraction size of 500 ul. The collected tube contains still 5 mg Na-ascorbate.

Result of purification with HPLC

|  | Activity [MBq] | % | Collection time [min] | Volume [µl] |
| --- | --- | --- | --- | --- |
| Injected activity | 378 | 100 |  | 80 |
| Remainder eppendorf tube | 30 | 8 |  |  |
| Fraction 3 | 120 | 31 | 12.5-13.0 | 500 |
| Fraction 4 | 180 | 48 | 13.0-13.5 | 500 |

Preparation of the labeled peptid for mouse i.v. injection

The two fractions have been fused and the solvent was evaporated during 35 min.

Afterwards 600 ul PBS 1× with 10 ul 5 mM DTPA solution was added.

Final solution: 295 MBq/610 ul.

Stability

12 MBq of the radiolabelled compound was incubated in 2 mL fresh human plasma. A 40 µL probe was taken after 0, 1, 2, 18, 24, 48 and 72 h and added 200 µL (50% Methanol and 50% Acetonitril) in a Mini-UniPrep Filter. The solution is filtered after vortexing. 40 µL of the filtered solution is analyzed by HPLC.

Biodistribution Studies

CD1 nu/nu mice were injected with $5×10^6$ A431 cells. CCK-2 receptor positive A431 cells' were injected into one flank and mock cells on the other as an unspecific control. The tumors reach a weight of about 80 to 120 mg after about 10 days. 150-200 kBq (5 pmol) of the radiolabelled peptides were injected into the tail vein. Mice were killed by $CO_2$ asphyxiation after defined time points post injection. The organs were dissected, weighted and the activity was measured. The % injected activity per gram (% i.A./g) was calculated. The animal experiments were approved by the local animal welfare committee and performed according to national regulations.

DISCUSSION

1. Aloj L, Caraco C, Panico M, Zannetti A, Del Vecchio S, Tesauro D, De Luca S, Arra C, Pedone C, Morelli G, Salvatore M. In vitro and in vivo evaluation of 111In-DTPAGlu-G-CCK8 for cholecystokinin-B receptor imaging. *J Nucl Med.* 2004; 45(3):485-494.
2. Lehenberger S, Barkhausen C, Cohrs S, Fischer E, Grunberg J, Hohn A, Koster U, Schibli R, Turler A, Zhernosekov K. The low-energy beta(−) and electron emitter (161)Tb as an alternative to (177)Lu for targeted radionuclide therapy. *Nucl Med Biol.*38(6):917-924.

The invention claimed is:

1. A method of treating CCK-2 receptor associated diseases in a subject in need thereof, wherein the method comprises the step of administering a mini-gastrin analogue having the formula:
   X-DGlu-DGlu-DGlu-DGlu-DGlu-DGlu-Ala-Tyr-Gly-Trp-Y-Asp-Phe-$NH_2$,
   wherein Y is an amino acid replacing methionine and X is a chemical group attached to the peptide for the purpose of therapeutic intervention at CCK-2 receptor associated diseases, to the subject, and wherein the CCK-2 receptor associated disease is selected from CCK-2 receptor positive tumors.
2. The method according to claim 1, wherein the CCK-2 receptor positive tumor is selected from medullary thyroid carcinomas (MTC), small cell lung cancers (SCLC), astrocytomes and stromal ovarial tumors.
3. The method according to claim 1, wherein Y is a methionine isosteric amino acid with no oxidation potential.
4. The method according to claim 1, wherein Y is norleucine.
5. The method according to claim 1 or 4, wherein X is a chelator for radiometals complexed with a radionuclide.
6. The method according to claim 5, wherein the chelator for radiometals is DOTA.
7. The method according to claim 5, wherein the radionuclide is selected from the group consisting of $^{177}$Lu, $^{90}$Y and $^{111}$In.
8. The method according to claim 1 or 2, wherein the mini-gastrin analogue is:
   DOTA-DGlu-DGlu-DGlu-DGlu-DGlu-DGlu-Ala-Tyr-Gly-Trp-Nle-Asp-Phe-$NH_2$.
9. The method according to claim 8, wherein the DOTA-DGlu-DGlu-DGlu-DGlu-DGlu-DGlu-Ala-Tyr-Gly-Trp-Nle-Asp-Phe-$NH_2$ is labelled with $^{177}$Lu.
10. The method according to claim 1, wherein X is an optically active chemical compound.
11. The method according to claim 1, wherein X is a chemotherapeutic active compound.
12. The method according to claim 1, wherein X is a nanoparticle or a liposome which has a therapeutic function by itself or which is loaded with an active compound.

* * * * *